US012793846B2

(12) United States Patent
Warngren et al.

(10) Patent No.: US 12,793,846 B2
(45) Date of Patent: Nov. 10, 2026

(54) COMPUTER-IMPLEMENTED METHOD FOR OPERATING A SEPARATION OR SYNTHESIS INSTRUMENT

(71) Applicant: Biotage AB, Uppsala (SE)

(72) Inventors: Anders Warngren, Uppsala (SE); Johan Jacksén, Vällingby (SE); Philip Lamberstam, Uppsala (SE); Caroline Wärn, Uppsala (SE); Fahim Hadj, Uppsala (SE); Jeanette Lagerholm, Järfälla (SE)

(73) Assignee: Biotage AB, Uppsala (SE)

( * ) Notice: Subject to any disclaimer, the term of this patent is extended or adjusted under 35 U.S.C. 154(b) by 225 days.

(21) Appl. No.: 18/888,867

(22) Filed: Sep. 18, 2024

(65) Prior Publication Data

US 2025/0307360 A1 Oct. 2, 2025

(30) Foreign Application Priority Data

Apr. 2, 2024 (SE) .................................... 2450350-0

(51) Int. Cl.
*G16H 40/67* (2018.01)
*G06F 3/14* (2006.01)
*G06F 21/31* (2013.01)

(52) U.S. Cl.
CPC ........... *G16H 40/67* (2018.01); *G06F 3/1423* (2013.01); *G06F 21/31* (2013.01)

(58) Field of Classification Search
None
See application file for complete search history.

(56) References Cited

U.S. PATENT DOCUMENTS 7,686,959 B2 * 3/2010 Horsman ............... G01N 30/34 210/143
8,041,437 B2 10/2011 Stellari et al.
10,008,965 B2 * 6/2018 Priem ....................... H02P 9/04
10,990,261 B2 4/2021 Sreenivasan et al.
11,550,275 B2 * 1/2023 Maddern ............... G05B 15/02
(Continued)

FOREIGN PATENT DOCUMENTS

CN 209231774 U 8/2019
CN 211506725 U 9/2020
CN 211606971 U 9/2020

OTHER PUBLICATIONS

Swedish Search Report dated Oct. 1, 2024 issued in corresponding Swedish Patent Application No. 2450350-0.

*Primary Examiner* — Henry Orr
(74) *Attorney, Agent, or Firm* — Harness, Dickey & Pierce, P.L.C.

(57) ABSTRACT

A computer-implemented method for operating an instrument being a separation instrument or a synthesis instrument, which includes a sample operation device and a computing device for controlling the sample operation device, is disclosed. The method involves displaying a first graphical user interface for controlling the instrument on a display device of the computing device, transmitting information corresponding to a second graphical user interface for controlling the instrument to a remote computing device connected to the computing device via a network interface, and setting the first graphical user interface to an observer mode in which controlling the instrument is limited to a halt function for halting a process of the sample operation device.

18 Claims, 7 Drawing Sheets

(56) References Cited

U.S. PATENT DOCUMENTS

| | | | | |
|---|---|---|---|---|
| 12,661,188 | B2 * | 6/2026 | Oberkircher | A61B 34/25 |
| 2002/0075160 | A1 * | 6/2002 | Racz | G08C 17/00<br>340/5.74 |
| 2008/0256227 | A1 | 10/2008 | Malin | |
| 2011/0136684 | A1 * | 6/2011 | Heiner | B01J 19/0046<br>506/7 |
| 2012/0010475 | A1 | 1/2012 | Rossmeier et al. | |
| 2015/0242395 | A1 | 8/2015 | Hodak | |
| 2016/0363917 | A1 * | 12/2016 | Blackley | G06F 3/0488 |

* cited by examiner

COMPUTER-IMPLEMENTED METHOD FOR OPERATING A SEPARATION OR SYNTHESIS INSTRUMENT

RELATED APPLICATIONS

This application claims priority to Swedish Patent Application No. 2450350-0, filed on Apr. 2, 2024, the entire contents of which are incorporated herein by reference.

The present patent disclosure relates to the field of separation and/or synthesis instruments, specifically to computer-implemented methods and systems for operating and controlling such instruments.

Instruments, such as separation or synthesis instruments, are widely used in various fields, including pharmaceuticals, biotechnology, and chemical industries, for the synthesis, analysis, separation, and purification of samples. These instruments often require control and/or monitoring to ensure accurate results and maintain safety within the (laboratory) environment in which these instruments are situated. For example, a flash chromatography instrument requires one or more solvents which should be present in sufficient amounts.

An example separation instrument is a chromatography instrument, for example the flash chromatography instrument mentioned above, a high-performance liquid chromatography (HPLC) instrument, or a gas chromatography (GC) instrument. One example of a synthesis instrument is a peptide synthesis instrument.

In recent years, there has been a growing trend towards remote control of instruments via computers on a network, such as the internet. This allows researchers and technicians to operate and monitor the instruments from a remote location, providing increased flexibility and efficiency in research and development operations. However, remote control of instruments also presents certain challenges and potential safety concerns.

The remote user controlling the instrument may not always have a complete understanding of the local (laboratory) environment and any safety issues that may arise during operation. This lack of situational awareness can lead to accidents or damage to the instrument if the remote user is unable to quickly respond to an emergency or recognize a potential safety hazard.

Thus, there is a need for improved systems and methods for remote control of instruments that address these safety concerns and provide local personnel with the ability to intervene in case of an emergency or malfunction.

According to a first aspect of the disclosure, a computer-implemented method for operating an instrument is provided. The instrument may be a separation instrument or a synthesis instrument. The instrument comprises a sample operation device and a computing device for controlling the sample operation device. The method comprises displaying a first graphical user interface for controlling the instrument on a display device of the computing device. The method also includes transmitting, via a network interface of the computing device, information corresponding to a second graphical user interface for controlling the instrument to a remote computing device connected to the computing device. The first graphical user interface is set to an observer mode in which controlling the instrument is limited to a halt function for halting a process of the sample operation device. This aspect allows for remote control of the instrument while maintaining a level of control at the local level through the halt function.

In some examples, the instrument is a laboratory instrument.

In some examples, the instrument includes the ability to perform measurement techniques such as optical transmission/reflection/absorption or optical spectroscopy, etc., on samples or (intermediate) products such as eluents and/or eluates.

The sample operation device is a part of the instrument which performs an operation or process on or with a sample, or a selected sample from a plurality of samples. The operation can be anything related to separation or synthesis, for example. As an example, the operation may include obtaining at least a part of the sample from a sample container, providing the obtained sample to a chromatography column, and/or receiving one or more products from the column in one or more respective product containers.

Remote control of instruments has the potential for conflicting instructions to be sent to the instrument by multiple users. To address this issue, lock out the local interface of the instrument when a remote user is connected can be done, placing the local interface in a view-only mode. While this approach can prevent conflicting instructions, it also creates a potential safety concern, as local personnel may be unable to intervene in case of an emergency or malfunction. The halt function alleviates this issue.

Optionally in some examples, the sample operation device is configured to receive a multi-sample holder and to process a selected sample of the multi-sample holder. The multi-sample holder may be configured to hold multiple sample containers. The sample containers may be, for example, test tubes, (reaction) vials or cuvettes. The reaction vials may, for example, be suitable for microwave synthesis. The cuvettes may be suitable for optical experiments. The sample operation device may be configured to take sample out of the sample containers.

Optionally in some examples, the method further comprises receiving, at the computing device, an activation of the halt function from the first graphical user interface and halting the process of the sample operation device in response to the activation of the halt function. This provides an additional level of control and safety, as the process can be halted immediately if necessary.

Optionally in some examples, the halt function for halting the process of the sample operation device is a stop function for stopping the process of the sample operation device.

Optionally in some examples, the halt function for halting the process of the sample operation device is a pause function for pausing the process of the sample operation device.

Optionally in some examples, the method provides access to a resume function in the first graphical user interface after the halt function is activated. This allows for the process to be resumed after it has been halted. This can be done, for example, if the issue is resolved after actions taken by the one present at the instrument who activated the halt function. The resume function avoids or lowers the chance of the process performed on the sample failing.

Optionally in some examples, access to the resume function is only provided after the computing device receives a command via the first graphical user interface to take control of the instrument. This provides an additional level of safety and quality of the results coming from the instrument.

Optionally in some examples, the method comprises providing a request for conformation of taking control of the instrument on the first graphical user interface when an actuation of the resume function is received by the computing device via the first graphical user interface.

Optionally in some examples, the method further comprises receiving, at the computing device, a resume command from the first graphical user interface and resuming the process of the sample operation device in response to the resume command. This provides a user-friendly interface for controlling the operation of the instrument.

Optionally in some examples, the method provides access to a stop function in the first graphical user interface after the halt function is activated, wherein the stop function allows irreversible stopping of the process. This provides a safety feature that allows for the irreversible stop of the process if necessary.

Optionally in some examples, the method further comprises receiving, at the computing device, a stop command from the first graphical user interface and irreversibly stopping the process of the sample operation device in response to the stop command. This provides a user-friendly interface for controlling the operation of the instrument.

Optionally in some examples, access to the stop function is only provided after the computing device receives a command via the first graphical user interface to take control of the instrument.

Optionally in some examples, the method comprises providing a request for conformation of taking control of the instrument on the first graphical user interface when an actuation of the stop function is received by the computing device via the first graphical user interface.

Optionally in some examples, the first graphical user interface displays real-time instrument status information. This provides the user with up-to-date information about the status of the instrument, allowing for more informed decision-making.

Optionally in some examples, the method further comprises storing user login credentials in a memory of the computing device.

Optionally in some examples, the method further comprises allowing a user to log in on the computing device via the first graphical user interface using first user login credentials; when a user is logged in on the computing device, requesting second user login credentials when the remote computing device attempts to take control of the instrument; and only allowing the remote computing device to control the instrument when first user login credentials are the same as the second user login credentials.

Optionally in some examples, access to the resume and stop function is only provided to a user with user login credentials that are the same as the first user login credentials.

Optionally in some examples, in addition to the first and second user login credentials, login credentials associated with a device owner or device admin result in an allowance of the remote computing device or the computing device to control the instrument.

Optionally in some examples, the display device is a touch display, and the method further comprises processing touch input from the touch display to control the computing device and the sample operation device. This provides a user-friendly and intuitive interface for controlling the instrument.

Optionally in some examples, the separation instrument is a chromatographic instrument, such as a flash chromatography instrument, a high-performance liquid chromatography (HPLC) instrument, or a gas chromatography (GC) instrument. This provides flexibility in the type of instrument that can be controlled using the method.

Other examples of separation instruments are sample preparation instruments, which may perform extraction methods and/or other sample preparation techniques.

Optionally in some examples, the synthesis instrument is a peptide synthesis instrument or an organic synthesis instrument.

Optionally in some examples, the synthesis device is a microwave synthesis device configured to use a microwave source as a heat source.

Optionally in some examples, the sample operation device comprises a pump configured to pump a solvent, and a solvent inlet configured to receive the solvent. This allows for the processing of samples using a variety of methods, increasing the versatility of the instrument.

According to a second aspect of the disclosure, an instrument is provided. The instrument may be a separation instrument or a synthesis instrument. The instrument comprises a sample operation device configured to process a sample and a computing device configured to control the sample operation device. The computing device comprises a processor, memory, a display device, and a network interface configured to exchange data with a remote computing device. The memory stores instructions that, when executed by the processor cause the processor to display a first graphical user interface for controlling the sample operation device on the display device, transmit information corresponding to a second graphical user interface for controlling the instrument to the remote computing device via the network interface, and set the first graphical user interface to an observer mode in which the controlling of the instrument is limited to a halt function for halting a process of the instrument. This aspect provides a instrument that can be controlled both locally and remotely, providing flexibility and control in the operation of the instrument.

Optionally in some examples, the instructions further cause the processor to receive an activation of the halt function from the first graphical user interface and halt the process of the sample operation device in response to the activation of the halt function. This provides an additional level of control and safety, as the process can be halted immediately if necessary.

Optionally in some examples, the instructions further cause the processor to provide access to a resume function in the first graphical user interface after the halt function is activated and receive a resume command from the first graphical user interface, and resume the process of the sample operation device in response to the resume command. This allows for the process to be resumed after it has been halted, providing flexibility and control over the operation of the instrument.

Optionally in some examples, the instructions further cause the processor to provide access to a stop function in the first graphical user interface after the halt function is activated, wherein the stop function allows irreversible stopping of the process, and receive a stop command from the first graphical user interface, and irreversibly stop the process of the sample operation device in response to the stop command. This provides a safety feature that allows for the immediate and irreversible stop of the process if necessary.

Optionally in some examples, the display device is a touch display, and the computing device is further configured to process touch input from the touch display to control the computing device and the sample operation device. This provides a user-friendly and intuitive interface for controlling the instrument.

Optionally in some examples, the memory further stores login credentials, and the computing device is configured to allow a user to log in on the computing device via the first graphical user interface, wherein only the user that is logged in on the computing device is allowed to control the instrument from the remote computing device. This provides a secure method for controlling the instrument, as only authorized users can control the instrument.

Optionally in some examples, the first graphical user interface comprises real-time instrument status information. This provides the user with up-to-date information about the status of the instrument, allowing for more informed decision-making.

Optionally in some examples, the sample operation device comprises a pump configured to pump a solvent, and a solvent inlet configured to receive the solvent. This allows for the processing of samples using a variety of methods, increasing the versatility of the instrument.

Optionally in some examples, the separation device is a chromatographic instrument, such as a flash chromatography instrument, a high-performance liquid chromatography (HPLC) instrument, or a gas chromatography (GC) instrument. This provides flexibility in the type of instrument that can be controlled using the method.

According to a third aspect of the disclosure, a system is provided that comprises the instrument and the remote computing device. This aspect provides a complete system for controlling a instrument both locally and remotely, providing flexibility and control in the operation of the instrument. This system can be used in a variety of laboratory settings, making it a versatile solution for laboratory instrument control.

According to a fourth aspect of the disclosure, there is provided an instrument, being a separation instrument or synthesis instrument, comprising:

- a sample operation device configured to process a sample; and
- a computing device configured to control the sample operation device, wherein the computing device comprises a processor, memory, a display device, an audio output device, and a network interface configured to exchange data with a remote computing device,
- the memory storing instructions that, when executed by the processor cause the processor to:
  - display, on the display device, of a first graphical user interface for controlling the sample operation device;
  - transmit, by the computing device to the remote computing device via the network interface, information corresponding to a second graphical user interface for controlling the instrument; and
  - when the remote computing device is in control of the instrument, providing one or more alerts comprising a visual alert on the first graphical interface or an audible alert using the audio output device, the one or more alerts indicating a remote computing device has control of the instrument.

The one or more alerts provides users present in the lab with information that a new user is controlling the instrument clarifying that the instrument may start an operation and that care should be taken, for example not to be too close to the instrument or not to open the instrument, etc. This provides an increased safety in the environment in which the instrument is present, such as a laboratory environment.

The one or more alerts may be provided only when a user starts a process with the instrument. In this case, the starting of the process may be delayed by a delay time such that anyone present near the instrument has time to take action.

BRIEF DESCRIPTION OF THE DRAWINGS

Examples are described in more detail below with reference to the appended drawings, of which.

DETAILED DESCRIPTION

The detailed description set forth below provides information and examples of the disclosed technology with sufficient detail to enable those skilled in the art to practice the disclosure.

Figure 1:
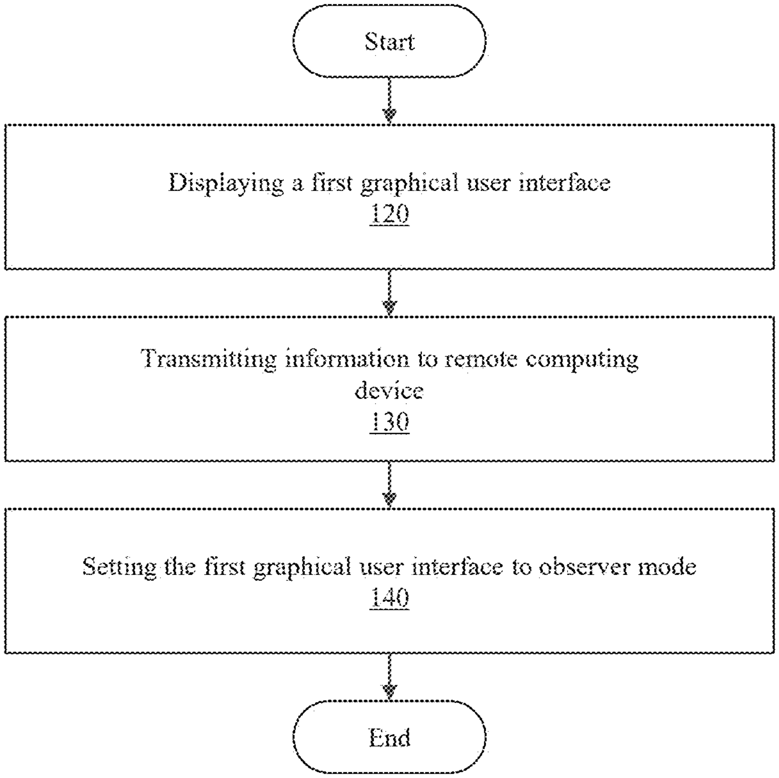
FIG. 1 is a flowchart illustrating an example of a computer-implemented method for operating the instrument.

In one implementation, FIG. 1 illustrates a computer-implemented method for operating a instrument 400. The method may include an optional step performing an operation on or with the sample, including operations related to separation of a sample or related to producing the sample, by the sample operation device 410. The sample processing may be any process that is performed by instruments that utilize a graphical user interface for controlling the instrument.

The method includes a step 120 of displaying a first graphical user interface 900 on a display device 426 of a computing device 420. The first graphical user interface 900 is designed to control the instrument 400, which includes a sample operation device 410.

The method includes a step 130 of transmitting information corresponding to a second graphical user interface for controlling the instrument 400 to a remote computing device 490. This transmission is facilitated via network interface 428 of the computing device 420. The remote computing device 490 is connected to the computing device 420, allowing for remote control of the instrument 400.

Furthermore, the method includes setting the first graphical user interface 900 to an observer mode. In this mode, the control of the instrument 400 is limited to a halt function. This function allows for halting a process of the sample operation device 410. The observer mode is particularly useful when the instrument 400 is being controlled from the remote computing device 490, ensuring that local control is limited to functions such as halting the process.

In some configurations, multiple remote computing devices can connect to the instrument. In this case, only one device can be in control of the instrument. This can be either the computing device of the instrument or one of the connected remote computing devices. For example, a user may connect with a laptop to the instrument and later with a desktop computer to the instrument. A message box can be presented to a newly connecting remote computing device, asking a user whether this remote computing device is to take control of the instrument. Control may be limited to the same user that is logged in on the instrument itself, optionally also including users with administrator rights.

Figure 2:
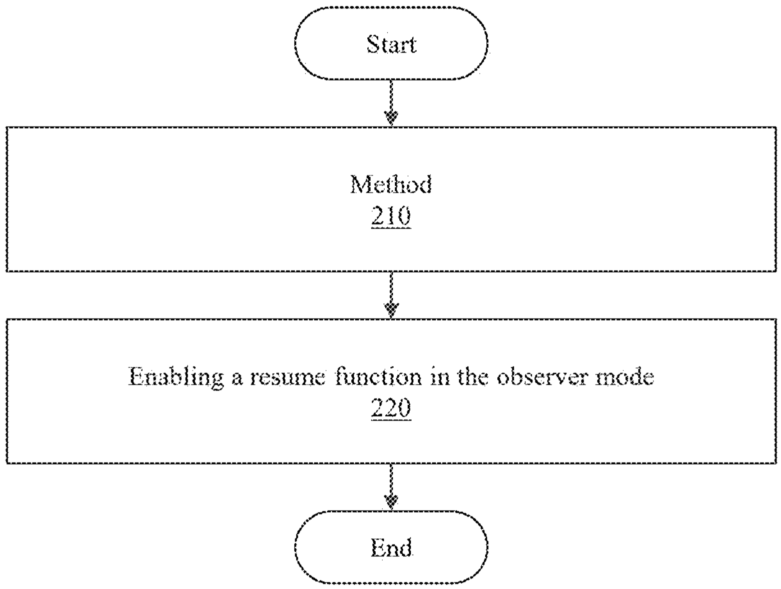
FIG. 2 is a flowchart illustrating an example of a computer-implemented method for operating the instrument.

In some configurations, the computer-implemented method shown in FIG. 2 expands upon the method described in FIG. 1, indicated as "method 210", by including a step 220 of enabling a resume function. After the halt function has been activated in the first graphical user interface 900, access to a resume function is provided. This function allows for the resumption of the halted process of the sample operation device 410.

The activation of the resume function is received at the computing device 420 through the first graphical user interface 900. In response to the activation of the resume function, the process of the sample operation device 410 is resumed. This feature provides flexibility in controlling the instrument 400, allowing for processes to be paused and resumed as needed.

Figure 3:
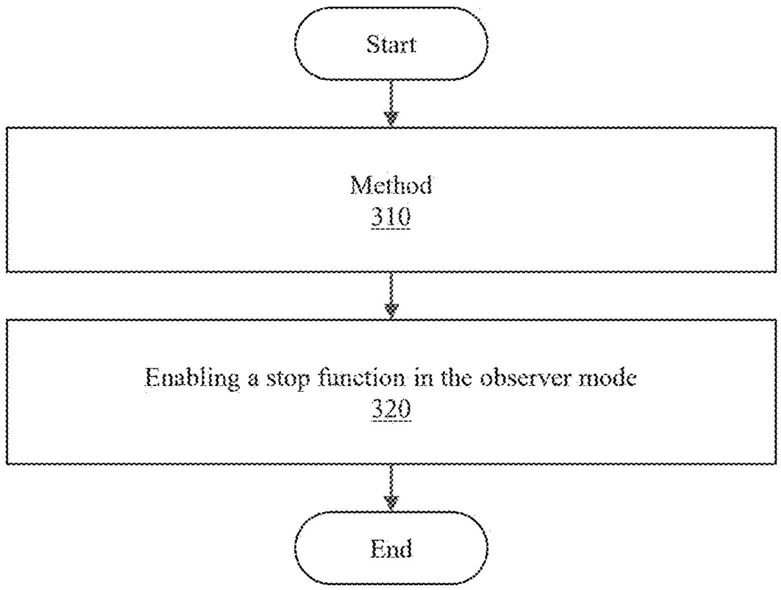
FIG. 3 is a flowchart illustrating an example of a computer-implemented method for operating the instrument.

In some examples, as shown in FIG. 3, the computer-implemented method described in FIG. 1 and/or FIG. 2, indicated as "method 310", may be further extended upon by including a stop function. After the halt function has been activated in the first graphical user interface 900, access to a stop function is provided. This function allows for the irreversible stopping of the process of the sample operation device 410.

The activation of the stop function is received at the computing device 420 through the first graphical user interface 900. In response to the activation of the stop function, the process of the sample operation device 410 is irreversibly stopped. This feature provides an additional level of control over the instrument 400, allowing for processes to be permanently stopped when necessary.

Figure 4:
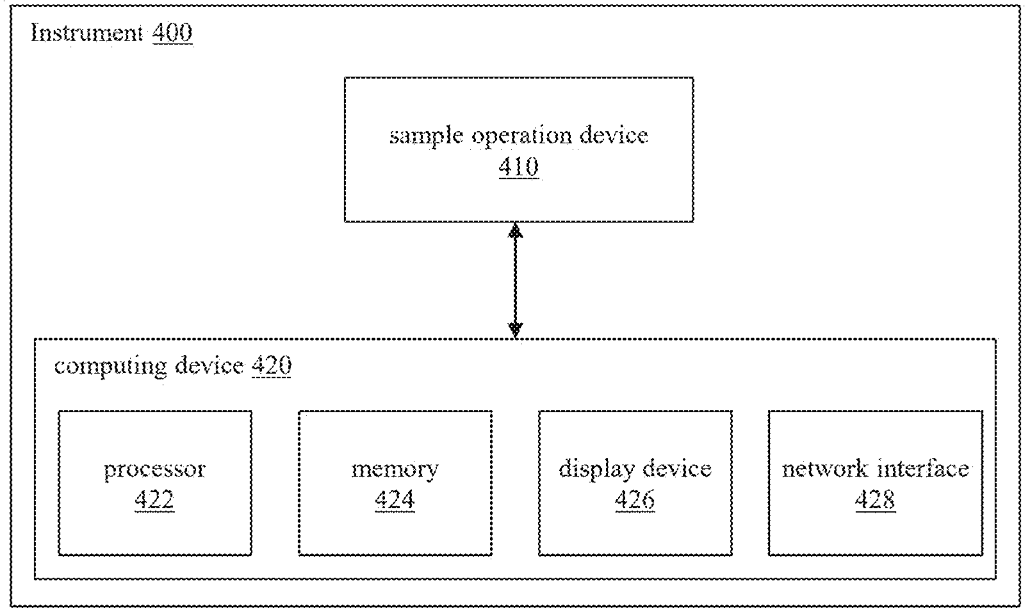
FIG. 4 is a block diagram illustrating an example of a instrument.

In FIG. 4 one configuration of the instrument 400 is provided. The instrument 400 comprises a sample operation device 410 and a computing device 420. The sample operation device 410 is configured to process a sample. The computing device 420, on the other hand, is configured to control the sample operation device 410 based upon input received by a user interacting with the graphical user interface locally or remotely. The computing device 420 includes a processor 422, memory 424, a display device 426, and a network interface 428. The memory 424 stores instructions that, when executed by the processor 422, cause the processor 422 to display the first graphical user interface 900 on the display device 426, transmit information to the remote computing device 490 via the network interface 428, and set the first graphical user interface 900 to an observer mode.

In some examples, the computing device 420 comprises first communication circuitry (not shown) for communicating with the sample operation device 410. The sample operation device 410 may comprise second communication circuitry for communicating with the first communication circuitry. The first and second communication circuitry may, for example, be implemented as serial communication, such as via the USB standard, parallel communication, ethernet, a message-based protocol, such as a controller area network (CAN bus), or the like. Alternatively, the network interface 428 may be configured to communicate with the sample operation device 410. The sample operation device 410 may in that case be provided with a corresponding network interface.

In one example, the second communication circuitry is a component of the sample operation device 410. The second communication circuitry is configured to communicate with the first communication circuitry of the computing device 420. The second communication circuitry transmits data to the computing device 420 and receives data, including control information, from the computing device 420. This communication allows the computing device 420 to control the operation of the sample operation device 410.

In some examples, the halt function is a feature of the first graphical user interface 900. When the first graphical user interface 900 is set to observer mode, the control of the instrument 400 is limited to the halt function, as described below in relation to FIG. 6 and FIG. 7A. The halt function allows for halting a process of the sample operation device 410. This function is accessible even when the first graphical user interface 900 is locked in observer mode (FIG. 7A). The halt function also enables access to the resume function and the stop function.

In one configuration, the computing device 420 is a component of the instrument 400. The computing device 420 is configured to control the sample operation device 410. The computing device 420 includes a processor 422, memory 424, a display device 426, and a network interface 428. The computing device 420 may communicate with the sample operation device 410 via the first communication circuitry.

In some examples, the processor 422 is a component of the computing device 420. The processor 422 executes the instructions stored in the memory 424. The execution of these instructions results in the display of the first graphical user interface 900 on the display device 426, the transmission of information to the remote computing device 490 via the network interface 428, and the setting of the first graphical user interface 900 to an observer mode.

In one implementation, the memory 424 is a component of the computing device 420. The memory 424 stores the instructions that are executed by the processor 422. The memory 424 may also store login credentials. This may be temporary storage, for example in RAM memory, in case the login credentials are stored elsewhere in the network to which the instrument is connected. These credentials allow a user to log in on the computing device 420 via the first graphical user interface 900. In one implementation, only the user that is logged in on the computing device 420 is allowed to control the instrument 400 from the remote computing device 490.

In some configurations, the display device 426 is a component of the computing device 420. The display device 426 displays the first graphical user interface 900 for controlling the instrument 400. In some examples, the display device 426 is a touch display device. The touch display device processes touch input from the touch display to control the computing device 420 and/or the sample operation device 410.

In one example, the network interface 428 is a component of the computing device 420. The network interface 428 is configured to exchange data with the remote computing device 490. This exchange of data allows the remote computing device 490 to control the instrument 400. The remote computing device 490 may be in the same local area network (LAN) to which the network interface 428 is connected. The remote computing device 490 may also connect to the network interface 428 via the internet, for instance using a virtual private network service.

In some implementations, the first communication circuitry is a component of the computing device 420. The first communication circuitry is configured to communicate with the second communication circuitry of the sample operation device 410. This communication allows the computing device 420 to control the operation of the sample operation device 410.

In one configuration, the instructions are stored in the memory 424 of the computing device 420. When executed by the processor 422, these instructions cause the processor 422 to display the first graphical user interface 900 on the display device 426, transmit information to the remote computing device 490 via the network interface 428, and set the first graphical user interface 900 to an observer mode. The instructions also include the halt function, and optionally the resume function, and/or the stop function.

Figure 7A:
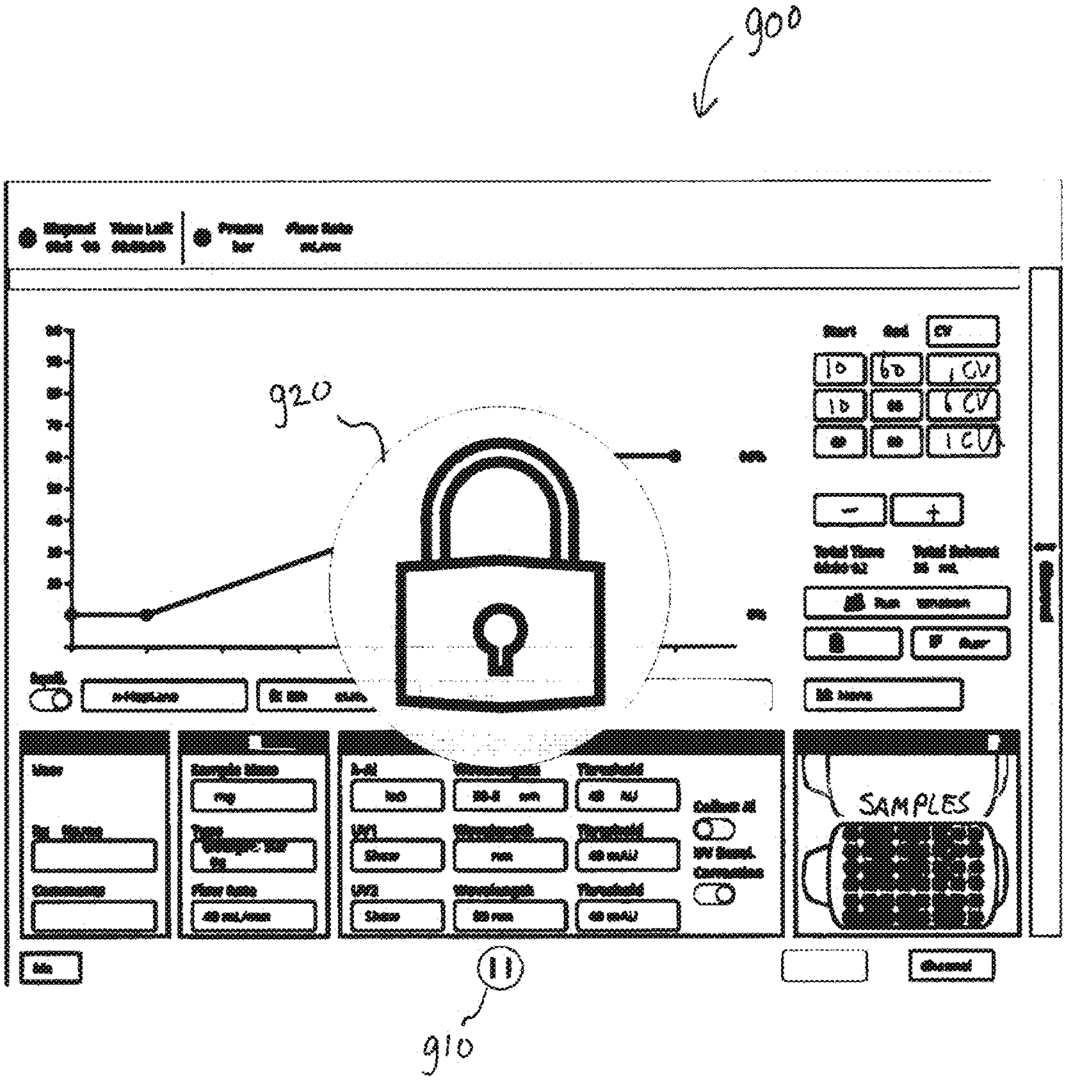
FIG. 7A is a schematic representation of an example of a first graphical user interface for controlling the instrument in observer mode.
Figure 7B:
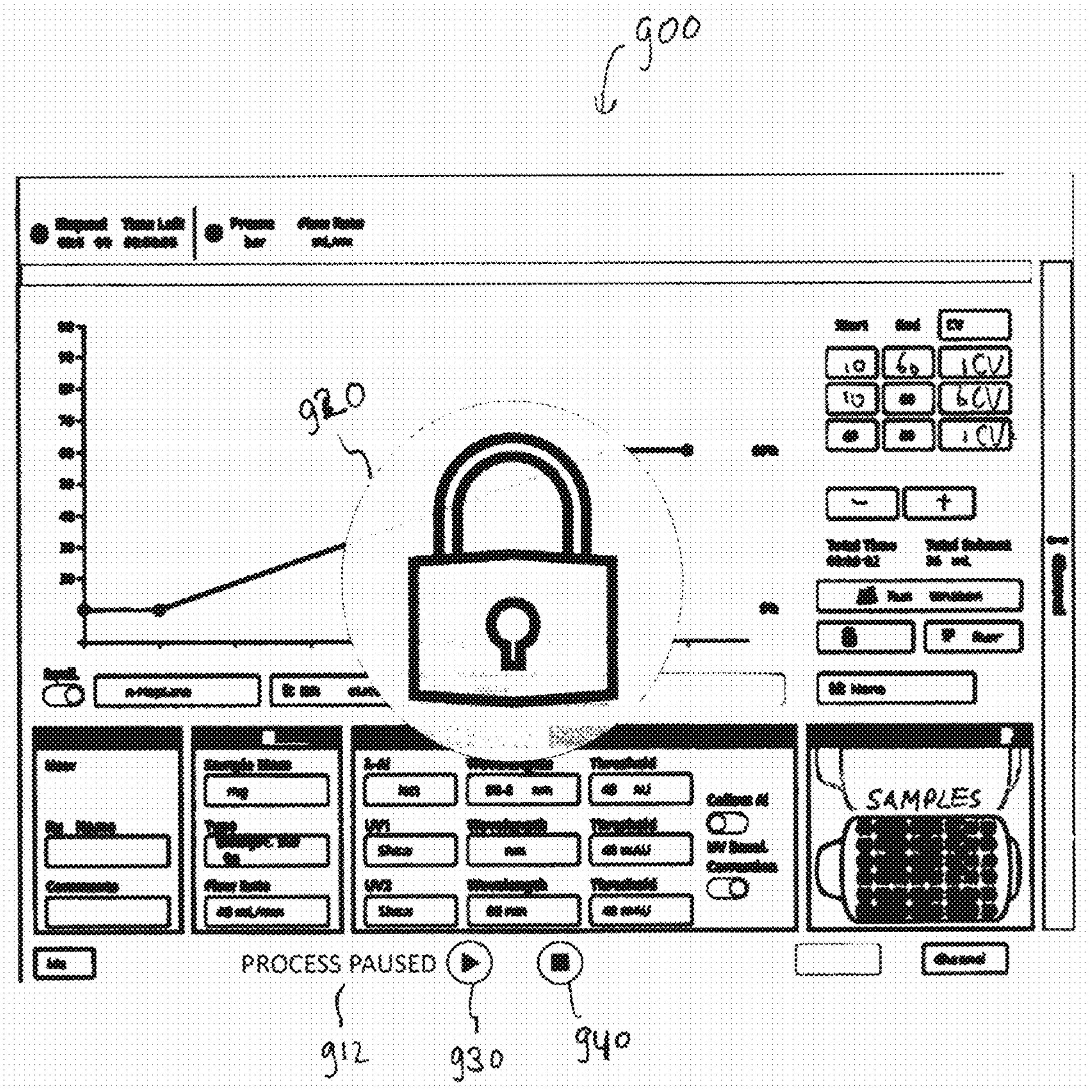
FIG. 7B is a schematic representation of an example of a first graphical user interface for controlling the instrument in observer mode.

In some examples, the resume function is a feature of the instructions stored in the memory 424. After the halt function has been activated in the first graphical user interface 900, the resume function is made accessible (FIG. 7B). The activation of the resume function is received at the computing device 420 through the first graphical user interface 900. In response to the activation of the resume function, the process of the sample operation device 410 is resumed.

Figure 6:
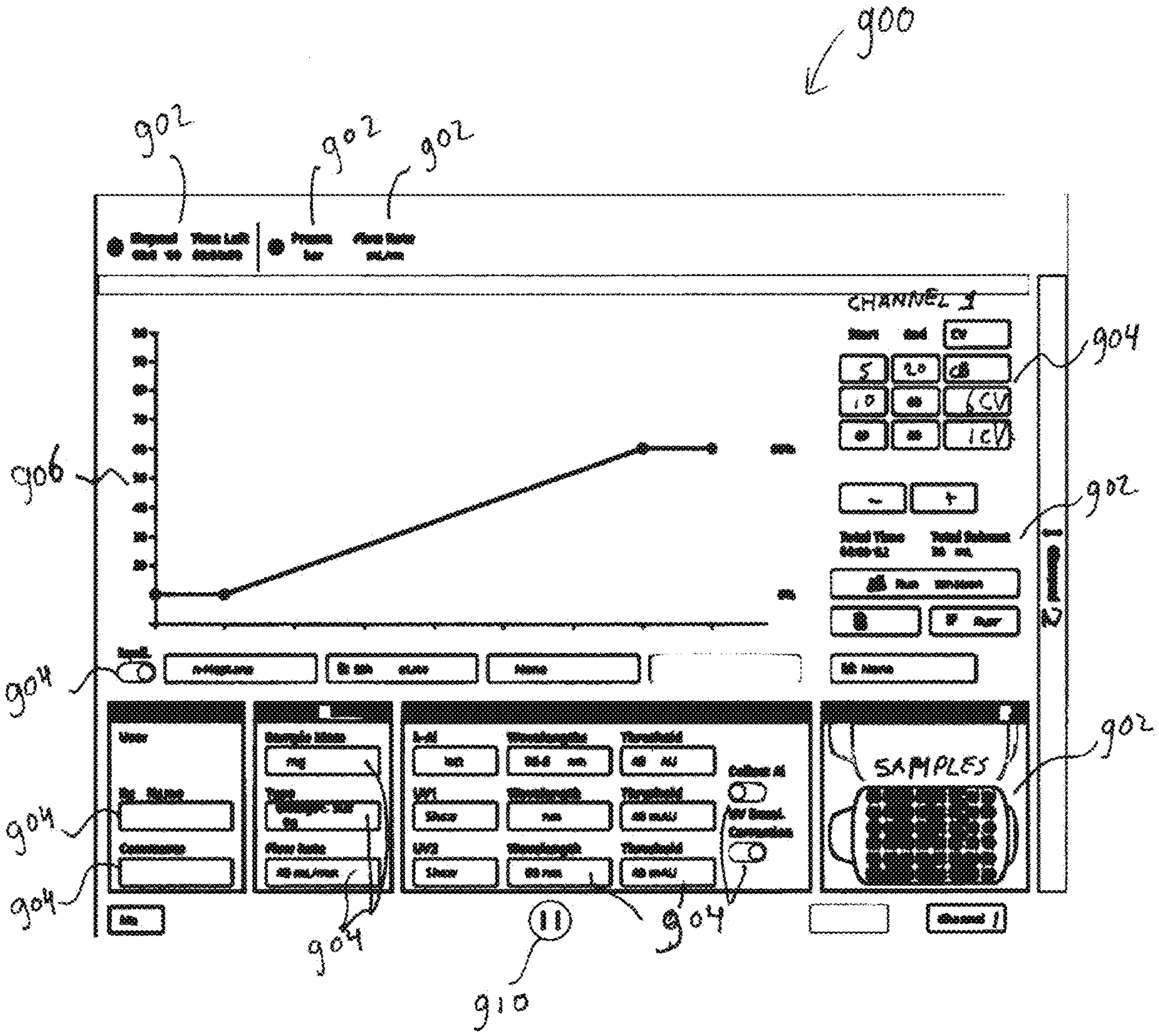
FIG. 6 is a schematic representation of an example of a first graphical user interface for controlling the instrument.

In one implementation, a first graphical user interface 900 as shown in FIG. 6 is displayed on the display device 426 of the computing device 420. The first graphical user interface 900 comprises various information fields 902, control fields 904, and a graph 906. The first graphical user interface 900 is designed to control the instrument 400. In FIG. 6, the first graphical user interface 900 is in a run mode in which a process is running, and a halt button 910 is shown. The halt button 910 is configured to activate the halt function when the user activates the halt button 910, for example by clicking the halt button 910 using a mouse or touching the halt button 910 when the display device 426 is a touch display device. In the run mode, control of the first graphical user interface 900 is allowed when the device is controlled locally.

When the remote computing device connects and takes control of the instrument, the first graphical user interface 900 is set to observer mode, and the control of the instrument 400 via the first graphical user interface 900 is limited to the halt button 910 as shown in FIG. 7A. In other words, even when the first graphical user interface 900 is locked in observer mode, the halt function remains accessible via the halt button 910. The halt button 910, when pressed such that the halt function is activated, may enable access to the resume function and the stop function.

The first graphical user interface 900 in the observer mode may comprise an observer mode indicator 920 that indicates that control of the instrument via the first graphical user interface 900 is locked. The observer mode indicator 920 may be indicated partially transparent such that the underlying information is still visible, or may be indicated in a place such that there is no overlap with other information of the process indicated by the first graphical user interface 900.

The first graphical user interface 900 also provides access to the resume function and the stop function after the halt function has been activated, an example of which is indicated in FIG. 7B. The text 912 "PROCESS PAUSED" is indicated in this example to indicate that the process is paused after the halt function is activated. Also, a resume button 930 and a stop button 940 are indicated in this example. The resume button 930 is for activating the resume function. The stop button 940 is for activating the stop function.

In some configurations, the stop function is a feature of the instructions stored in the memory 424. After the halt function has been activated in the first graphical user interface 900, the stop function is made accessible via the stop button 940. The activation of the stop function is received at the computing device 420 through the first graphical user interface 900. In response to the activation of the stop function, the process of the sample operation device 410 is irreversibly stopped.

Figure 8:
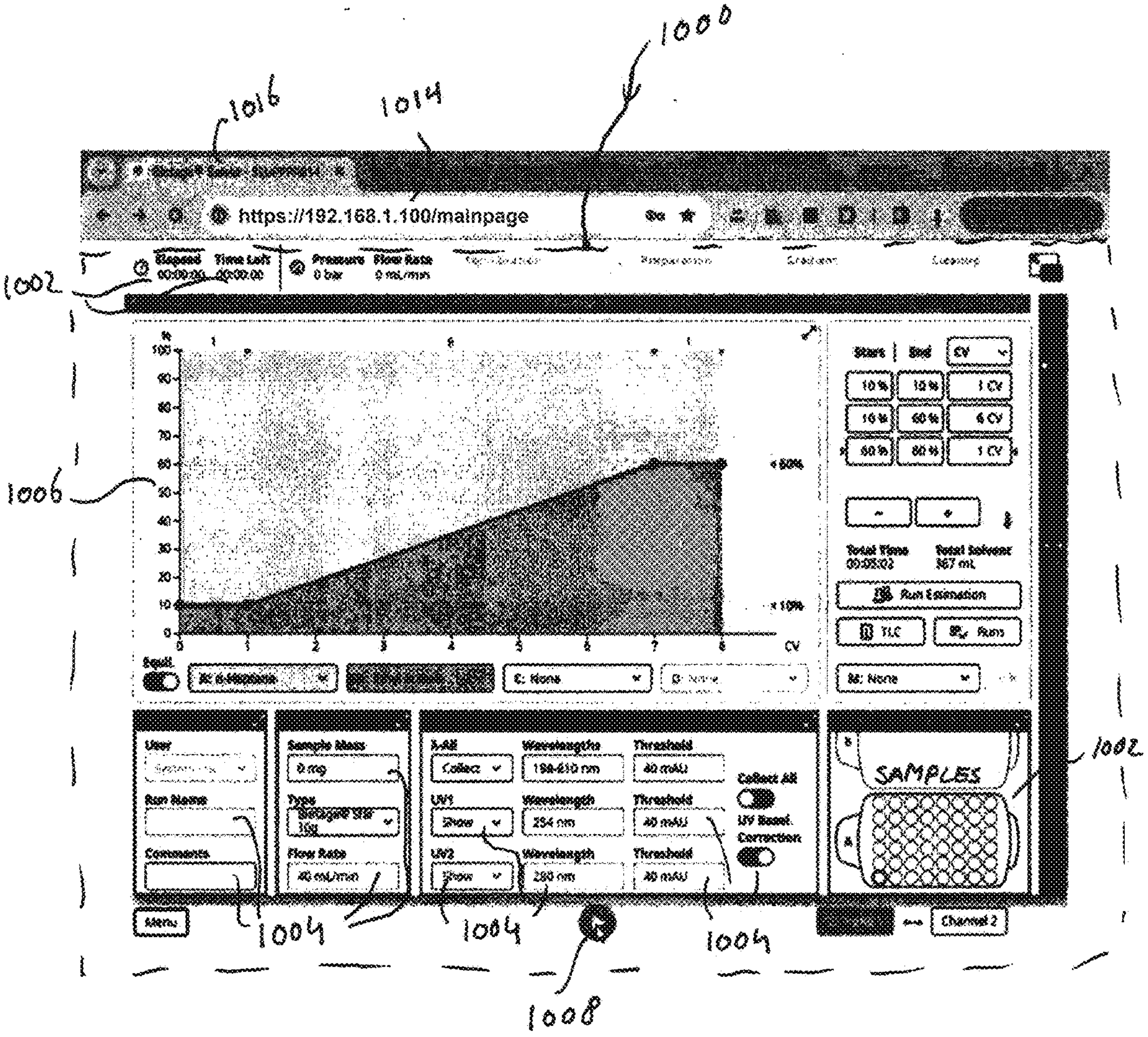
FIG. 8 is a schematic representation of an example of a second graphical user interface for controlling the instrument.

FIG. 8 provides a schematic representation of an example of a second graphical user interface 1000 for controlling the instrument 400. The second graphical user interface 1000 is shown in a web browser tab 1016, and is accessible by entering a correct address in the browser address line 1014. The second graphical user interface 1000 is displayed on a display device of or connected to the remote computing device 490.

The information corresponding to the second graphical user interface 1000 is transmitted from the computing device 420 of the instrument 400 to the remote computing device 490 via the network interface 428. The second graphical user interface 1000 allows for the remote control of the instrument 400 from the remote computing device 490.

In one implementation, the second graphical user interface 1000 comprises various information fields 1002, control fields 1004, and a graph 1006. The second graphical user interface 1000 is designed to control the instrument 400, and may be the same as the first graphical user interface 900, unless stated otherwise. In FIG. 8, the second graphical user interface 1000 is in an idle mode in which no process is running, and a start button 1008 is shown. When the start button 1008 is activated, the process is run by the instrument according to the settings provided by the user into the second graphical user interface 1000.

In one implementation, the sample operation device 410 is a component of the instrument 400. It is configured to process the sample. The sample operation device 410 may be a separation device which includes a pump and a solvent inlet. When the instrument is controlled remotely, the user may be unaware of the state of the solvents, for example. The solvent bottles may be (almost) empty or they may not be correctly inserted in the sample operation device. This is one example of an unsafe or unwanted operation of the instrument, as it will lead to erroneous results and/or wrongly processed samples.

The sample operation device 410 may be a flash chromatography instrument, a high-performance liquid chromatography (HPLC) instrument, or a gas chromatography (GC) instrument.

In some configurations, the pump is a component of the sample operation device 410. The pump is configured to pump a solvent. The solvent is used in the process of the sample in the sample operation device. In some implementations, the solvent inlet is a component of the sample operation device 410. The solvent inlet is configured to receive a solvent. The solvent is used in the process of the sample in the sample operation device 410. The solvent is pumped by the pump, which is also a component of the sample operation device 410.

Figure 5:
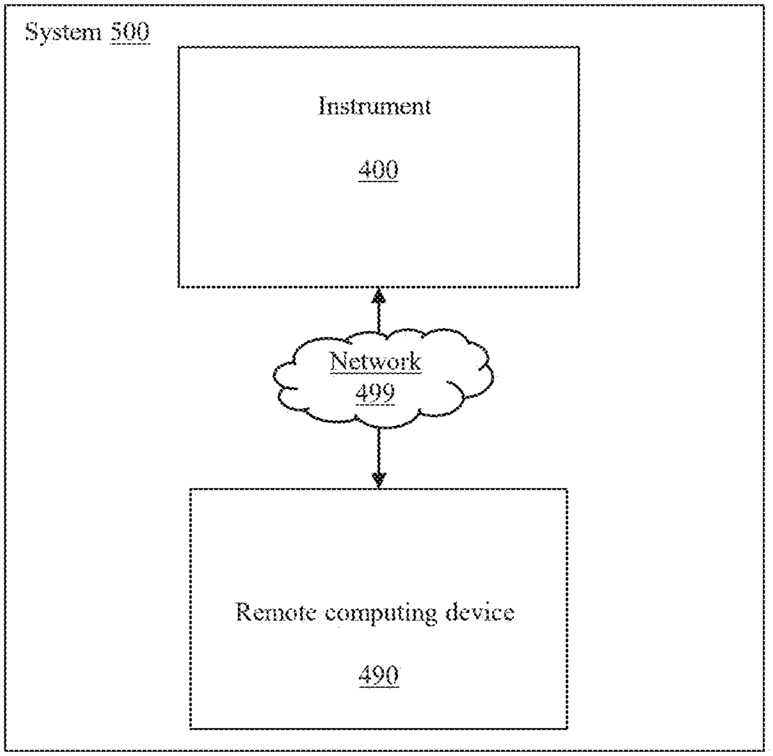
FIG. 5 is a block diagram illustrating an example of a system comprising the instrument and the remote computing device.

In one example, FIG. 5 presents a block diagram illustrating a system 500 that includes the instrument 400 and the remote computing device 490. The instrument 400 comprises the sample operation device 410 and the computing device 420. The computing device 420 is configured to control the sample operation device 410 and includes a network interface 428 for exchanging data with the remote computing device 490. This system allows for the remote control of the instrument 400 from the remote computing device 490.

According to some examples, when the remote computing device is in control of the instrument, providing one or more alerts comprising a visual alert on the first graphical interface or an audible alert using an audio output device, the one or more alerts indicating a remote computing device has control of the instrument. The computing device may comprise the audio output device or may at least be able to send a signal to the audio output device for outputting the audio alert. The audio alert may comprise one or more beeps, for example.

The disclosure comprises the following examples:

1. A computer-implemented method for operating an instrument being a separation instrument or a synthesis instrument, the instrument comprising a sample operation device and a computing device for controlling thew sample operation device, wherein the method comprises:

displaying a first graphical user interface for controlling the instrument on a display device of the computing device;

transmitting, via a network interface of the computing device, information corresponding to a second graphical user interface for controlling the instrument to a remote computing device connected to the computing device; and setting the first graphical user interface to an observer mode in which controlling the instrument is limited to a halt function for halting a process of the sample operation device.

2. The computer-implemented method of example 1, further comprising:

receiving, at the computing device, an activation of the halt function from the first graphical user interface; and halting the process of the sample operation device in response to the activation of the halt function.

3. The computer-implemented method of example 1, wherein the halt function for halting the process of the sample operation device is a stop function for stopping the process of the sample operation device.

4. The computer-implemented method of example 1, wherein the halt function for halting the process of the sample operation device is a pause function for pausing the process of the sample operation device.

5. The computer-implemented method of example 4, further comprising:

providing access to a resume function in the first graphical user interface after the halt function is activated.

6. The computer-implemented method of example 5, wherein access to the resume function is only provided after the computing device receives a command via the first graphical user interface to take control of the instrument.

7. The computer-implemented method of example 4, further comprising:

providing access to a stop function in the first graphical user interface after the halt function is activated, wherein the stop function allows irreversible stopping of the process.

8. The computer-implemented method of example 7, wherein access to the stop function is only provided after the computing device receives a command via the first graphical user interface to take control of the instrument.

9. The computer-implemented method of example 1, further comprising:

allowing a user to log in on the computing device via the first graphical user interface using first user login credentials, when a user is logged in on the computing device, requesting second user login credentials when the remote computing device attempts to take control of the instrument; and only allowing the remote computing device to control the instrument when first user login credentials are the same as the second user login credentials.

10. The computer-implemented method of example 1, wherein the display device is a touch display, and the method further comprises:

processing touch input from the touch display to control the computing device and the sample operation device.

11. The computer-implemented method of example 1, wherein the instrument is a chromatography instrument, such as a flash chromatography instrument, a high-performance liquid chromatography (HPLC) instrument, or a gas chromatography (GC) instrument.

12. The computer-implemented method of example 1, wherein the instrument is the separation instrument, wherein the sample operation device comprises a pump configured to pump a solvent, and a solvent inlet configured to receive the solvent.

13. Separation instrument comprising:

a sample operation device configured to process a sample; and a computing device configured to control the sample operation device, wherein the computing device comprises a processor, memory, a display device, and a network interface configured to exchange data with a remote computing device, the memory storing instructions that, when executed by the processor cause the processor to:

display, on the display device, of a first graphical user interface for controlling the sample operation device;

transmit, by the computing device to the remote computing device via the network interface, information corresponding to a second graphical user interface for controlling the separation instrument; and set the first graphical user interface to an observer mode in which the controlling of the separation instrument is limited to a halt function for halting a process of the separation instrument.

14. The separation instrument of example 13, wherein the instructions further cause the processor to:

receive, at the computing device, an activation of the halt function from the first graphical user interface; and halt the process of the sample operation device in response to the activation of the halt function.

15. The separation instrument of example 14, wherein the instructions further cause the processor to:

provide access to a resume function in the first graphical user interface after the halt function is activated; and receive, at the computing device, a resume command from the first graphical user interface, and resume the process of the sample operation device in response to the resume command.

16. The separation instrument of example 14, wherein the instructions further cause the processor to:

provide access to a stop function in the first graphical user interface after the halt function is activated, wherein the stop function allows irreversible stopping of the process; and receive, at the computing device, a stop command from the first graphical user interface, and irreversibly stop the process of the sample operation device in response to the stop command.

17. The separation instrument of example 13, wherein the display device is a touch display, and the computing device is further configured to process touch input from the touch display to control the computing device and the sample operation device.

18. The separation instrument of example 13, wherein the memory further stores login credentials, and the computing device is configured to allow a user to log in on the computing device via the first graphical user interface, wherein only the user that is logged in on the computing device is allowed to control the separation instrument from the remote computing device.

19. The separation instrument of example 13, wherein the sample operation device comprises a pump configured to pump a solvent, and a solvent inlet configured to receive the solvent.

20. The separation instrument of example 13, wherein the sample operation device is a chromatography instrument, such as flash chromatography instrument, a high-performance liquid chromatography (HPLC) instrument, or a gas chromatography (GC) instrument.

21. Synthesis instrument comprising:

a sample operation device configured to process a sample; and a computing device configured to control the sample operation device, wherein the computing device comprises a processor, memory, a display device, and a network interface configured to exchange data with a remote computing device, the memory storing instructions that, when executed by the processor cause the processor to:

display, on the display device, of a first graphical user interface for controlling the sample operation device;

transmit, by the computing device to the remote computing device via the network interface, information corresponding to a second graphical user interface for controlling the synthesis instrument; and set the first graphical user interface to an observer mode in which the controlling of the synthesis instrument is limited to a halt function for halting a process of the synthesis instrument.

22. The synthesis instrument of example 21, wherein the instructions further cause the processor to:

receive, at the computing device, an activation of the halt function from the first graphical user interface; and halt the process of the sample operation device in response to the activation of the halt function.

23. The synthesis instrument of example 21, wherein the instructions further cause the processor to:

provide access to a resume function in the first graphical user interface after the halt function is activated; and receive, at the computing device, a resume command from the first graphical user interface, and resume the process of the sample operation device in response to the resume command.

24. The synthesis instrument of example 21, wherein the instructions further cause the processor to:

provide access to a stop function in the first graphical user interface after the halt function is activated, wherein the stop function allows irreversible stopping of the process; and receive, at the computing device, a stop command from the first graphical user interface, and irreversibly stop the process of the sample operation device in response to the stop command.

25. The synthesis instrument of example 21, wherein the display device is a touch display, and the computing device is further configured to process touch input from the touch display to control the computing device and the sample operation device.

26. The synthesis instrument of example 21, wherein the memory further stores login credentials, and the computing device is configured to allow a user to log in on the computing device via the first graphical user interface, wherein only the user that is logged in on the computing device is allowed to control the synthesis instrument from the remote computing device.

27. The synthesis instrument of example 21, wherein the sample operation device comprises a pump configured to pump a solvent, and a solvent inlet configured to receive the solvent.

29. Separation instrument comprising:

a sample operation device configured to process a sample; and a computing device configured to control the sample operation device, wherein the computing device comprises a processor, memory, a display device, an audio output device, and a network interface configured to exchange data with a remote computing device, the memory storing instructions that, when executed by the processor cause the processor to:

display, on the display device, of a first graphical user interface for controlling the sample operation device;

transmit, by the computing device to the remote computing device via the network interface, information corresponding to a second graphical user interface for controlling the separation instrument; and when the remote computing device is in control of the separation instrument, providing one or more alerts comprising a visual alert on the first graphical interface or an audible alert using the audio output device, the one or more alerts indicating a remote computing device has control of the separation instrument.

30. Synthesis instrument comprising:

a sample operation device configured to process a sample; and a computing device configured to control the sample operation device, wherein the computing device comprises a processor, memory, a display device, an audio output device, and a network interface configured to exchange data with a remote computing device, the memory storing instructions that, when executed by the processor cause the processor to:

display, on the display device, of a first graphical user interface for controlling the sample operation device;

transmit, by the computing device to the remote computing device via the network interface, information corresponding to a second graphical user interface for controlling the synthesis instrument; and when the remote computing device is in control of the synthesis instrument, providing one or more alerts comprising a visual alert on the first graphical interface or an audible alert using the audio output device, the one or more alerts indicating a remote computing device has control of the synthesis instrument.

31. System comprising the separation instrument according to example 13 or example 29 and the remote computing device.

32. System comprising the synthesis instrument according to example 21 or example 30 and the remote computing device.

The terminology used herein is for the purpose of describing particular aspects only and is not intended to be limiting of the disclosure. As used herein, the singular forms "a," "an," and "the" are intended to include the plural forms as well, unless the context clearly indicates otherwise. As used herein, the term "and/or" includes any and all combinations of one or more of the associated listed items. It will be further understood that the terms "comprises," "comprising," "includes," and/or "including" when used herein specify the presence of stated features, integers, actions, steps, operations, elements, and/or components, but do not preclude the presence or addition of one or more other features, integers, actions, steps, operations, elements, components, and/or groups thereof.

It will be understood that, although the terms first, second, etc., may be used herein to describe various elements, these elements should not be limited by these terms. These terms are only used to distinguish one element from another. For example, a first element could be termed a second element, and, similarly, a second element could be termed a first element without departing from the scope of the present disclosure.

A person of skill in the art would readily recognize that steps of various above-described methods can be performed by programmed computers. Herein, some embodiments are also intended to cover program storage devices, e.g., digital data storage media, which are machine or computer readable and encode machine-executable or computer-executable programs of instructions, wherein said instructions perform some or all of the steps of said above-described methods. The program storage devices may be, e.g., digital memories, magnetic storage media such as a magnetic disks and magnetic tapes, hard drives, or optically readable digital data storage media. The embodiments are also intended to cover computers programmed to perform said steps of the above-described methods.

The functions of the various elements shown in the figures, including any functional blocks labelled as "units", "processors" or "modules", may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "unit", "processor" or "controller" should not be construed to refer exclusively to hardware capable of executing software, and may implicitly include, without limitation, digital signal processor (DSP) hardware, network processor, application specific integrated circuit (ASIC), field programmable gate array (FPGA), read only memory (ROM) for storing software, random access memory (RAM), and non-volatile storage. Other hardware, conventional and/or custom, may also be included. Similarly, any switches shown in the Figures are conceptual only. Their function may be carried out through the operation of program logic, through dedicated logic, or through the interaction of program control and dedicated logic, the particular technique being selectable by the implementer as more specifically understood from the context.

It should be appreciated by those skilled in the art that any block diagrams herein represent conceptual views of illustrative circuitry embodying the principles of the invention. Similarly, it will be appreciated that any flow charts, flow diagrams, state transition diagrams, pseudo code, and the like represent various processes which may be substantially represented in computer readable medium and so executed by a computer or processor, whether or not such computer or processor is explicitly shown.

Unless otherwise defined, all terms (including technical and scientific terms) used herein have the same meaning as commonly understood by one of ordinary skill in the art to which this disclosure belongs. It will be further understood that terms used herein should be interpreted as having a meaning consistent with their meaning in the context of this specification and the relevant art and will not be interpreted in an idealized or overly formal sense unless expressly so defined herein.

It is to be understood that the present disclosure is not limited to the aspects described above and illustrated in the drawings; rather, the skilled person will recognize that many changes and modifications may be made within the scope of the present disclosure and appended claims. In the drawings and specification, there have been disclosed aspects for purposes of illustration only and not for purposes of limitation, the scope of the disclosure being set forth in the following claims.

The invention claimed is:

1. A computer-implemented method for operating an instrument being a separation instrument or a synthesis instrument, the instrument comprising a sample operation device and a computing device for controlling the sample operation device, wherein the method comprises:

- displaying a first graphical user interface for controlling the instrument on a display device of the computing device;
- transmitting, via a network interface of the computing device, information corresponding to a second graphical user interface for controlling the instrument to a remote computing device connected to the computing device; and
- setting the first graphical user interface to an observer mode in which controlling the instrument is limited to a halt function for halting a process of the sample operation device,
  - wherein the halt function for halting the process of the sample operation device is a pause function for pausing the process of the sample operation device, and
  - wherein the method further comprises providing access to a stop function in the first graphical user interface in response to activating the halt function, wherein the stop function allows irreversible stopping of the process.

2. The computer-implemented method of claim 1, further comprising:

- receiving, at the computing device, an activation of the halt function from the first graphical user interface; and
- halting the process of the sample operation device in response to the activation of the halt function.

3. The computer-implemented method of claim 1, wherein the halt function for halting the process of the sample operation device is a stop function for stopping the process of the sample operation device.

4. The computer-implemented method of claim 1, wherein access to the stop function is only provided after the computing device receives a command via the first graphical user interface to take control of the instrument.

5. The computer-implemented method of claim 1, further comprising:

allowing a user to log in on the computing device via the first graphical user interface using first user login credentials, when a user is logged in on the computing device, requesting second user login credentials when the remote computing device attempts to take control of the instrument; and only allowing the remote computing device to control the instrument when first user login credentials are the same as the second user login credentials.

6. The computer-implemented method of claim 1, wherein the instrument is a chromatography instrument, such as a flash chromatography instrument, a high-performance liquid chromatography (HPLC) instrument, or a gas chromatography (GC) instrument.

7. The computer-implemented method of claim 1, wherein the instrument is the separation instrument, wherein the sample operation device comprises a pump configured to pump a solvent, and a solvent inlet configured to receive the solvent.

8. The computer-implemented method of claim 1, further comprising:

providing access to a resume function in the first graphical user interface after the halt function is activated.

9. The computer-implemented method of claim 8, wherein access to the resume function is only provided after the computing device receives a command via the first graphical user interface to take control of the instrument.

10. Instrument, being either a separation instrument or a synthesis instrument, comprising:

a sample operation device configured to process a sample; and a computing device configured to control the sample operation device, wherein the computing device comprises a processor, memory, a display device, and a network interface configured to exchange data with a remote computing device, the memory storing instructions that, when executed by the processor cause the processor to:

display, on the display device, of a first graphical user interface for controlling the sample operation device;

transmit, by the computing device to the remote computing device via the network interface, information corresponding to a second graphical user interface for controlling the instrument; and set the first graphical user interface to an observer mode in which the controlling of the instrument is limited to a halt function for halting a process of the instrument, wherein the halt function for halting the process of the sample operation device is a pause function for pausing the process of the sample operation device, and wherein instructions further comprise provide access to a stop function in the first graphical user interface in response to activating the halt function, wherein the stop function allows irreversible stopping of the process.

11. The instrument of claim 10, wherein the display device is a touch display, and the computing device is further configured to process touch input from the touch display to control the computing device and the sample operation device.

12. The instrument of claim 10, wherein the memory further stores login credentials, and the computing device is configured to allow a user to log in on the computing device via the first graphical user interface, wherein only the user that is logged in on the computing device is allowed to control the instrument from the remote computing device.

13. The instrument of claim 10, wherein the sample operation device comprises a pump configured to pump a solvent, and a solvent inlet configured to receive the solvent.

14. The instrument of claim 10, wherein the sample operation device is a chromatography instrument, such as flash chromatography instrument, a high-performance liquid chromatography (HPLC) instrument, or a gas chromatography (GC) instrument.

15. System comprising the instrument according to claim 10 and the remote computing device.

16. The instrument of claim 10, wherein the instructions further cause the processor to:

receive, at the computing device, an activation of the halt function from the first graphical user interface; and halt the process of the sample operation device in response to the activation of the halt function.

17. The instrument of claim 16, wherein the instructions further cause the processor to:

provide access to a resume function in the first graphical user interface after the halt function is activated; and receive, at the computing device, a resume command from the first graphical user interface, and resume the process of the sample operation device in response to the resume command.

18. The instrument of claim 16, wherein the instructions further cause the processor to:

receive, at the computing device, a stop command from the first graphical user interface, and irreversibly stop the process of the sample operation device in response to the stop command.

* * * * *